US011524017B2

(12) United States Patent
Chung et al.

(10) Patent No.: US 11,524,017 B2
(45) Date of Patent: Dec. 13, 2022

(54) METHOD OF USING SUBSTRATES OF AKR1B1/AKR1B10 AS ANTI-CANCER DRUGS

(71) Applicant: Beijing Normal University Hong Kong Baptist University United International College, Guangdong (CN)

(72) Inventors: Stephen Chung, Hong Kong (CN); Shiqing Zhang, Guangdong (CN)

(73) Assignee: Beijing Normal University Hong Kong Baptist University United International College, Guangdong (CN)

(*) Notice: Subject to any disclaimer, the term of this patent is extended or adjusted under 35 U.S.C. 154(b) by 0 days.

(21) Appl. No.: 15/772,579

(22) PCT Filed: Nov. 3, 2016

(86) PCT No.: PCT/US2016/060275
§ 371 (c)(1),
(2) Date: May 1, 2018

(87) PCT Pub. No.: WO2017/079402
PCT Pub. Date: May 11, 2017

(65) Prior Publication Data
US 2019/0091247 A1     Mar. 28, 2019

Related U.S. Application Data

(60) Provisional application No. 62/250,524, filed on Nov. 4, 2015.

(51) Int. Cl.
| | |
|---|---|
| *A61K 31/69* | (2006.01) |
| *A61K 38/05* | (2006.01) |
| *A61K 38/06* | (2006.01) |
| *A61K 31/11* | (2006.01) |
| *A61K 31/121* | (2006.01) |
| *A61K 31/191* | (2006.01) |
| *A61K 31/198* | (2006.01) |
| *A61K 31/4188* | (2006.01) |
| *A61K 31/4402* | (2006.01) |
| *A61K 31/57* | (2006.01) |
| *A61K 31/7004* | (2006.01) |
| *A61K 45/06* | (2006.01) |
| *A61K 31/19* | (2006.01) |
| *A61P 35/00* | (2006.01) |
| *A61K 38/55* | (2006.01) |

(52) U.S. Cl.
CPC .............. *A61K 31/69* (2013.01); *A61K 31/11* (2013.01); *A61K 31/121* (2013.01); *A61K 31/19* (2013.01); *A61K 31/191* (2013.01); *A61K 31/198* (2013.01); *A61K 31/4188* (2013.01); *A61K 31/4402* (2013.01); *A61K 31/57* (2013.01); *A61K 31/7004* (2013.01); *A61K 38/05* (2013.01); *A61K 38/06* (2013.01); *A61K 38/55* (2013.01); *A61K 45/06* (2013.01); *A61P 35/00* (2018.01)

(58) Field of Classification Search
CPC .... A61K 2300/00; A61K 31/11; A61K 31/69; A61K 31/121; A61K 31/19; A61K 31/191; A61K 31/198; A61K 31/4188; A61K 31/4402; A61K 31/57; A61K 31/7004; A61K 38/05; A61K 38/06; A61K 38/55; A61K 45/06; A61P 35/00
See application file for complete search history.

(56) References Cited

U.S. PATENT DOCUMENTS

| | | | | |
|---|---|---|---|---|
| 6,670,330 | B1* | 12/2003 | Lampidis | A61K 31/18 514/23 |
| 2003/0087951 | A1* | 5/2003 | Burman | A61K 9/0095 514/423 |
| 2007/0259956 | A1* | 11/2007 | Thompson | A61K 51/0491 514/529 |
| 2009/0163450 | A1* | 6/2009 | Hoffmann | A61P 35/00 514/161 |

FOREIGN PATENT DOCUMENTS

| | | |
|---|---|---|
| WO | 2011117453 A1 | 9/2011 |
| WO | 2015057175 A1 | 4/2015 |

OTHER PUBLICATIONS

Kapoor, S. "AKR1B10 and its emerging role in tumor carcinogenesis and as a cancer biomarker" Int. J. Cancer, 2013, vol. 132, pp. 495. (Year: 2013).*
Qin et al. "2-Doxyglucose sensitizes melanoma cells to TRAIL-induced apoptosis which is reduced by mannose" Biochemical and Biophysical Research Communications, 2010, vol. 401, issue 2, pp. 293-299. (Year: 2010).*
Ebert et al. "Proteasome inhibitors MG-132 and bortezomib induce AKR1C1, AKR1C3, AKR1B1, and AKR1B10 in human colon cancer cell lines SW-480 and HT-29" Chemico-Biological Interactions, 2011, vol. 191, issue 1-3, pp. 239-249. (Year: 2011).*
Bailey, H. "L-S,R-buthionine sulfoximene:historical development and clinical issues" Chemico-Biological Interactions, 1998, vol. 111-112, pp. 239-254. (Year: 1998).*
Zhao et al. "Selectivity determinants of inhibitor binding to the tumour marker human aldose reductase-like protein (AKR1B10) discovered from molecular docking and database screening" European Journal of Medicinal Chemistry, 2010, vol. 45, pp. 4354-4357. (Year: 2010).*

(Continued)

*Primary Examiner* — Umamaheswari Ramachandran
(74) *Attorney, Agent, or Firm* — Liang & Hennessey LLP; Stanley D. Liang

(57) ABSTRACT

The present disclosure relates to, inter alia, a method of treating cancer in a human patient in need thereof, comprising administering a therapeutically effective amount of a substrate of AKR1B1, AKR1B10, or both to said patient, wherein said patient has, or is suspected to have, cancer cells with elevated levels of AKR1B1, AKR1B10, or both, wherein said substrate is not 2-deoxy-D-glucose.

7 Claims, 11 Drawing Sheets

(56) References Cited

OTHER PUBLICATIONS

Yuan et al. (Oncogene, 2009, 28, 3775-3786). (Year: 2009).*
Shoeb, Curr Med Chem, 2014, 21(2), 230-237). (Year: 2014).*
Johnson et al., (British J. of Cancer 2001) (Year: 2001).*
Gura et al. (Science 1997) (Year: 1997).*
Cancer Drug Design and Discovery: Neidle, Stephen, ed. (Elsevier/Academic Press, 2008) (Year: 2008).*
Ellis et al. (Ann. Surg. Jul. 1990, p. 45-50) (Year: 1990).*
CAS Registry (1984) (Year: 1984).*
Zhao et al. (European Journal of Medicinal Chemistry, 2010, vol. 45, pp. 4354-4357) (Year: 2010).*
Abou Ghalia et al. (Clinical Biochemistry, 33, 8, 657-662, 2000) (Year: 2000).*
Ma, Int J Cancer, Sep. 15, 2012;131(6):E862-71 (Year: 2012).*
Ma et al. (The J of Biol. Chem, 283, 6, pp. 3418-3423, 2008) (Year: 2008).*
Riddick J H et al: "The effect of glyceraldehyde on glucose metabolism in Ehrlich ascites tumor cells", Biochemical Pharmacology, Elsevier, US, vol. 16, No. 2, Feb. 1, 1967 (Feb. 1, 1967), pp. 239-248, XP025498670,ISSN: 0006-2952, DOI: 10.1016/0006-2952(67)90026-3; [retrieved on Feb. 1, 1967] the whole document p. 239, paragraph 1. last sentence p. 246, Discussion.
Verma Malkhey et al: "Inhibiting wild-type and C299S mutant AKR1B10; a homologue of aldose reductase upregulated in cancers", European Journal of Pharmacology, vol. 584, No. 2, Feb. 5, 2008 (Feb. 5, 2008), pp. 213-221, XP028744255,ISSN: 0014-2999, DOI:10.1016/J.EJPHAR.2008.01.036 the whole document especially p. 220, section 4.3, 'AKR1B10 inhibitors as antineoplastic agents'.
Balendiran G K et al:: "Cancer biomarker AKR1B10 and carbonyl metabolism", Chemico-Biological Interactions, Elsevier Science Irland, IR, vol. 178, No. 1-3, Mar. 16, 2009 (Mar. 16, 2009), pp. 134-137, XP025909724, ISSN: 0009-2797, DOI: 10.1016/J.CBI.2008.10.044 [retrieved on Nov. 5, 2008] the whole document.
Ma, J; Cao, D: "Human aldo-keto reductases: structure, substrate specificity and roles in tumorigenesis", Biomolecular Concepts, vol. 2, No. 1-2, Jan. 1, 2011 (Jan. 1, 2011), pp. 115-126, XP009192955,ISSN: 1868-5021, DOI: 10.1515/bmc.2011.010 the whole document.
ISR received in PCT/US16/60275 dated Jan. 20, 2017, pp. 3.

* cited by examiner

Compare with NC group, * $P < 0.05$

HepG2 cell

SKOV3 cell

US 11,524,017 B2

METHOD OF USING SUBSTRATES OF AKR1B1/AKR1B10 AS ANTI-CANCER DRUGS

TECHNICAL FIELD

This invention relates to the field of cancer therapy.

BACKGROUND

Human AKR1B1 and AKR1B10 belong to a family of aldo-keto reductases. They both have 316 amino acids and their amino acid sequences are 71.4% identical to each other. They use NADPH as co-factor to reduce a wide range of substrates and they have similar substrate specificity. They can reduce, with varying degree of efficiency, a variety of low molecular weight aldehydes, including the aldehyde form of sugars. For unknown reason, these two enzymes were found to be over-expressed in a variety of cancers. AKR1B1 and AKR1B10 are over-expressed in 70-95% of the liver cancer. AKR1B10 is also over-expressed in other cancers, including prostate, breast, ovarian, cervical, rectal, lung and oral cancer.

SUMMARY

This disclosure provides a method of treating cancer in a human patient in need thereof, comprising administering a therapeutically effective amount of a substrate of AKR1B1, AKR1B10, or both, to the patient; the patient has, or is suspected to have, cancer cells with elevated levels of AKR1B1, AKR1B10, or both; and the substrate is not 2-deoxy-D-glucose. In certain embodiments, this method further comprises administering a therapeutically effective amount of an inhibitor of reduced glutathione (GSH) to the patient.

This disclosure also provides a method of treating cancer in a human patient in need thereof, comprising administering to the patient a therapeutically effective amount of an activator of AKR1B1 enzyme level or activity, AKR1B10 enzyme level or activity, or the enzyme level or activity of both, in a cancer cell; and administering a therapeutically effective amount of a substrate of AKR1B1, AKR1B10, or both, to the patient; the substrate is not 2-deoxy-D-glucose.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 1A is a graph of the survival rate of cancer cells treated with 2DG for 72 hours. Bars represent mean±SEM (n=5); **p<0.01 versus NC group. FIG. 1B shows comparison of expression levels of AKR1B1 and AKR1B10 in six kinds of cancer cells. Both AKR1B1 and AKR1B10 protein correspond to a 36-kDa band. Bottom band shows the same membrane re-probed for β-actin, which corresponds to a 42-kDa band. FIG. 1C is a graph showing quantitative analysis of band intensity relative to β-actin, bars represent mean±SEM (n=3).

FIG. 2A is a graph showing survival rate of HepG2 cells. FIG. 2B SKOV3 cells. FIG. 2C HCT116 cells. FIG. 2D CaCo2 cells. Bars represent mean±SEM (n=5); **p<0.01 versus only 2DG induced cells, *p<0.05 versus only 2DG induced cells.

FIG. 3A HepG2 and SKOV3 cells with or without fidarestat and tolrestat. FIG. 3B HCT116 and CaCo2 cells with or without fidarestat and tolrestat. Bars represent mean±SEM (n=5); Of p<0.01 versus NC group; **p<0.01 versus 2DG group.

FIG. 4A Sensitivity to 2DG of MG-132 treated cells. FIG. 4B Sensitivity to 2DG of bortezomib treated cells. FIG. 4C-FIG. 4F are western blot analysis of cells treated with MG-132 or bortezomid. Column charts represent band intensity relative to β-actin. Bars represent mean±SEM (n=3), p<0.01 versus 0-dose group. FIG. 4C MG-132 treated HT-29 cells. FIG. 4D MG-132 treated SW480 cells. FIG. 4E Bortezomib treated HT-29 cells. FIG. 4F Bortezomib treated SW480 cells.

FIG. 5A Cells treated with diacetyl. FIG. 5B Cells treated with glyceraldehyde. Bars represent mean±SEM (n=5); *p<0.05 versus NC group; p<0.01 versus NC group.

FIG. 7A. Enzyme activity expressed as the amount of NADPH (nmol) oxidized per min per mg of protein. FIG. 7B. Comparison of the toxicity of 2DG, diacetyl and glyceraldehyde, redrawn with part of the data from FIG. 1 and FIG. 5. Bars represent mean±SEM (n=5); ** p<0.01 versus 2DG group.

FIG. 8A. Effects of BSO on diacetyl toxicity, p<0.01 versus Dia (1.25 mM) group; ##p<0.01 versus Dia (0.625 mM) group. FIG. 8B. Effects of BSO on glyceraldehyde toxicity, p<0.01 versus Gly (1.25 mM) group; ##p<0.01 versus Gly (0.625 mM) group. FIG. 8C. Effects of NAC on diacetyl toxicity, **p<0.01 versus Dia (2.5 mM) group; ##p<0.01 versus Dia (1.25 mM) group. FIG. 8D. Effects of NAC on glyceraldehyde toxicity,

**p<0.01 versus Gly (2.5 mM) group; ##p<0.01 versus Gly (1.25 mM) group. Bars represent mean±SEM (n=5).

Figure 9A:
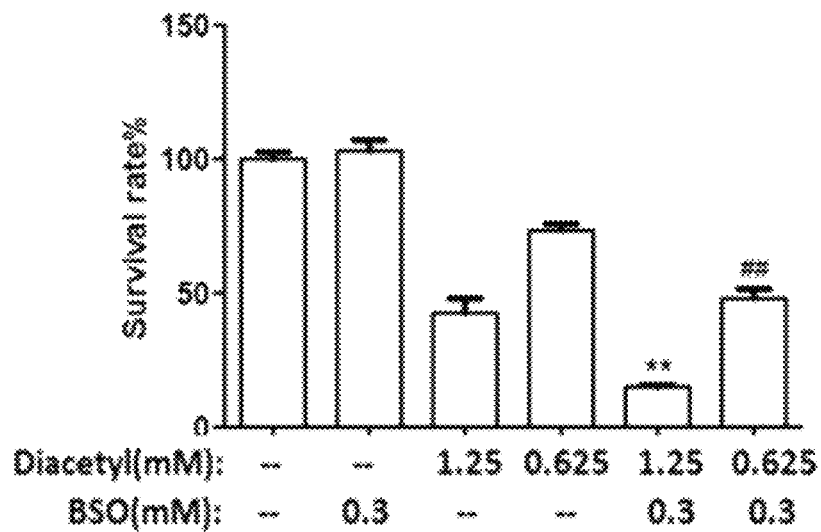
Figure 9A:
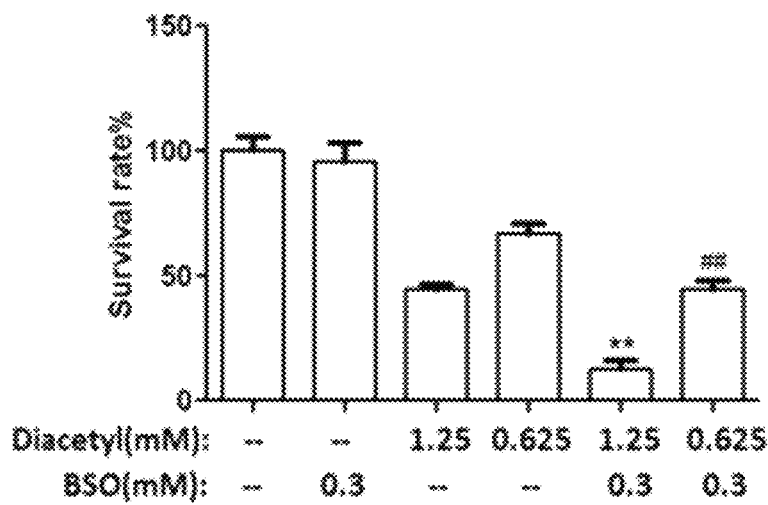
Figure 9B:
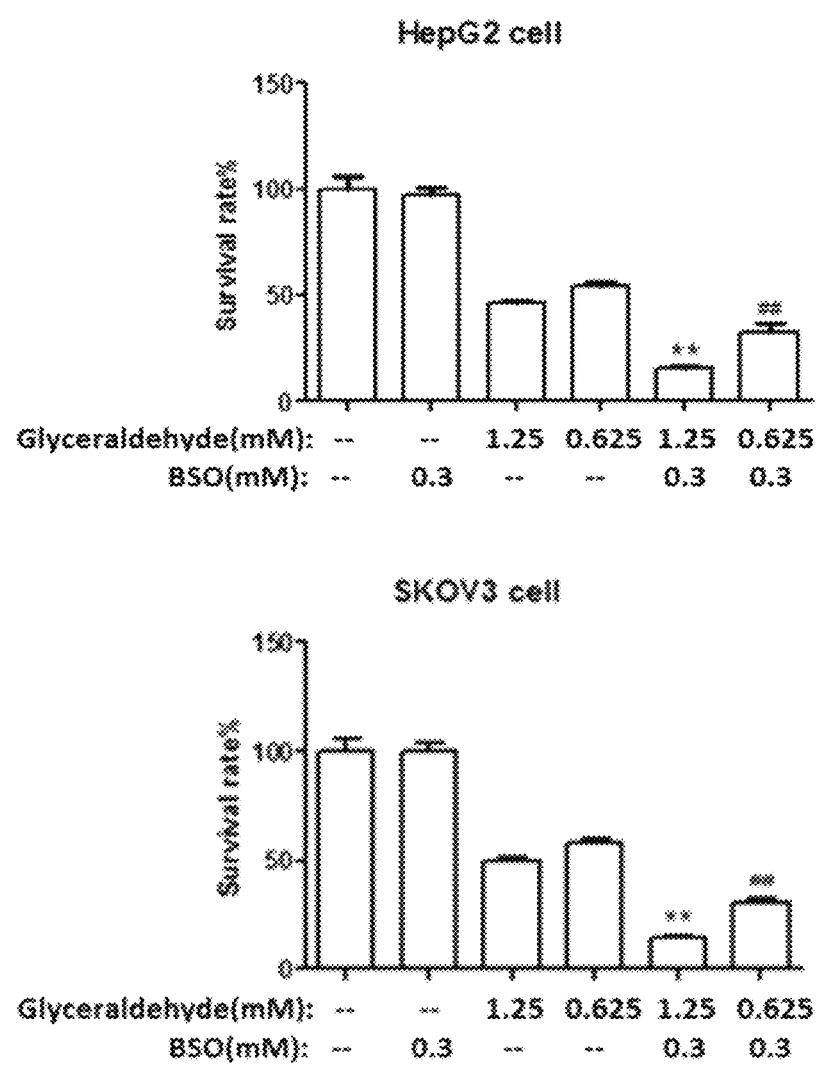

FIG. 9. FIG. 9A shows BSO exacerbates the toxicity of diacetyl. Compare with diacetyl 1.25 mM, P<0.01; Compare with diacetyl 0.625 mM, ##P<0.01. FIG. 9B shows BSO exacerbates the toxicity of glyceraldehyde. Compare with glyceraldehyde 1.25 mM, P<0.01; compare with glyceraldehyde 0.625 mM, ##P<0.01.

Figure 10:
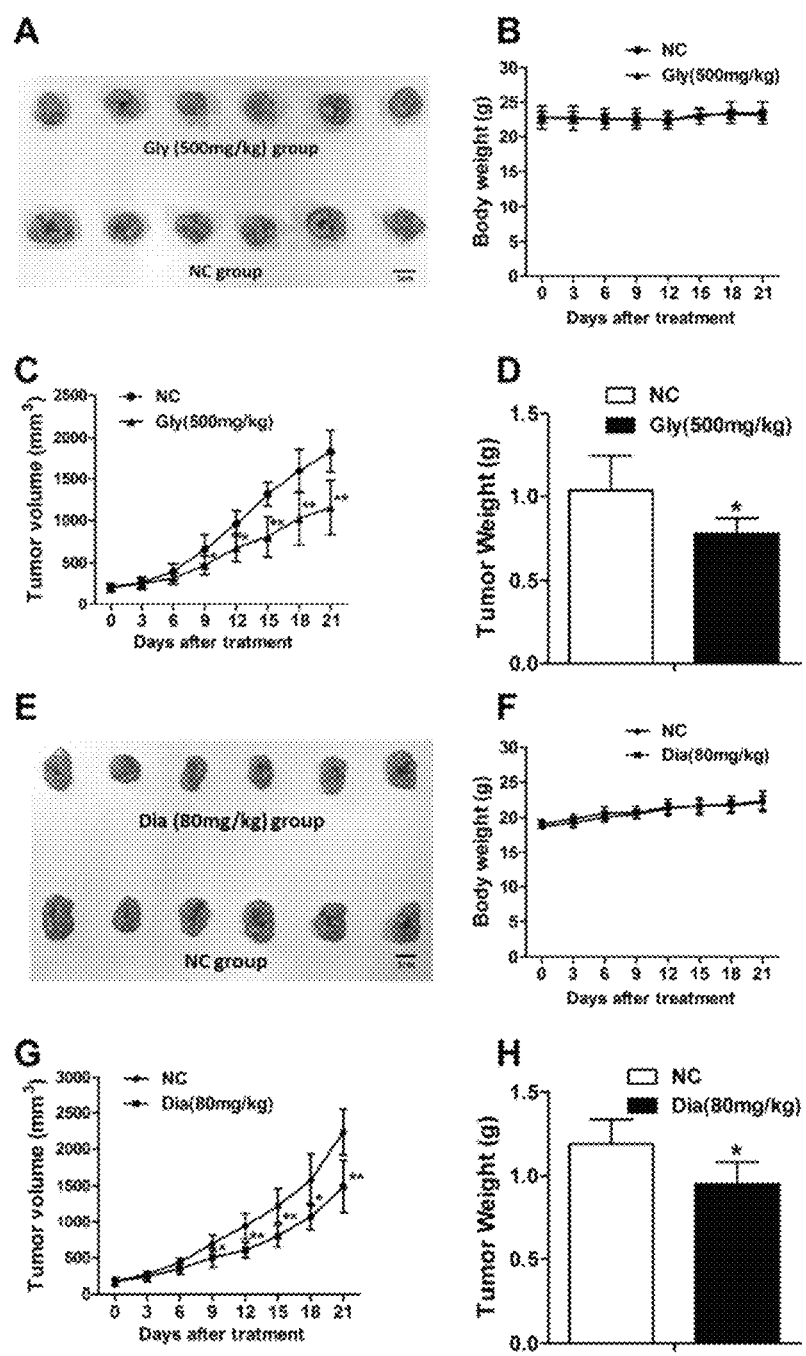

FIG. 10. The anti-cancer effect of glyceraldehyde and diacetyl on tumor xenograft model. Tumor volume was measured every 3 days (d) after implantation and treatment initiated when the tumor size is bigger than 2000 mm$^3$. Tumors were removed at the 21 day of treatment and their sizes and weights were evaluated. FIG. 10A. Picture of tumors after glyceraldehyde treatment. FIG. 10B. Body weight curve after glyceraldehyde treatment. FIG. 10C. Tumor volume after glyceraldehyde treatment. FIG. 10D. Tumor weight after glyceraldehyde treatment. FIG. 10E. Picture of tumors after diacetyl treatment. FIG. 10F. Body weight after diacetyl treatment. FIG. 10G. Tumor volume after diacetyl treatment. FIG. 10H. Tumor weight after diacetyl treatment. #p<0.05, ##p<0.01 versus NC group. Bars represent mean±SEM (n=6).

DETAILED DESCRIPTION

As used herein, the word "a" or "plurality" before a noun represents one or more of the particular noun. For example, the phrase "a mammalian cell" represents "one or more mammalian cells."

As used herein, the terms "subject" and "patient" are used interchangeably. A patient or a subject can be a human patient or a human subject.

The term "effective amount" or "a therapeutically effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease in a patient, or any other desired alteration of a biological system. An effective amount can be administered in one or more administrations.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

2-deoxyglucose (2DG) is a mild anticancer drug that is being used to augment other anticancer treatments. The cytotoxicity of 2DG is not as severe as some of the anticancer drugs such as doxorubicin or cisplatin. However, its specificity in killing cancer cells makes it a good candidate to enhance the efficacy of other cancer therapies. It has been shown to have synergistic effect in enhancing the killing of breast cancer cells by 5-fluorouracil, doxorubicin, cisplatin, cyclophosphamide, and herceptin. It enhances apoptosis of melanoma cells induced by TNF-related apoptosis ligands, and also enhances the apoptotic effect of several histone deacetylase inhibitors on breast, glioma and cervical cancer cells. 2DG also enhances radiation therapy. 2DG is thought to kill cancer specifically because cancer cells metabolize more glucose than normal cells, and 2DG, being a non-metabolizable glucose analog, is thought to inhibit glucose metabolism. However, 2DG only inhibits glycolysis by about 15-40%, not enough to cause glucose starvation. Further, it has been shown that 2-fluorodeoxy-D-glucose (2FDG), another non-metabolizable glucose analog that is a more potent glycolysis inhibitor than 2DG, is less effective than 2DG in killing some cancer cells. These observations suggested that 2DG does not kill cancer cells by inhibition of glucose metabolism as generally assumed.

2DG is a substrate for AKR1B1/AKR1B10. Human AKR1B1 (Aldo-keto reductase family 1, member B1 (aldose reductase)) and AKR1B10 (Aldo-keto reductase family 1, member B10 (aldose reductase-like enzyme)) belong to a family of aldo-keto reductases. They both have 316 amino acids and their amino acid sequences are 71.4% identical to each other. They use NADPH as co-factor to reduce a wide range of substrates and they have similar substrate specificity. They can reduce, with varying degree of efficiency, a variety of low molecular weight aldehydes, including the aldehyde form of sugars.

This disclosure discloses that 2DG kill cancer cells because of the increased oxidative stress generated when it is reduced by these two enzymes by the mechanism similar to glucose-induced oxidative stress in diabetes. AKR1B1 was first recognized as one of the major contributors to diabetic complications. It reduces glucose, which is elevated in diabetic patients, to sorbitol. In the process, its co-factor NADPH is depleted. NADPH is also the co-factor for glutathione reductase (GR), an enzyme that regenerates GSH (reduced glutathione) from GSSH (oxidized glutathione). Thus under hyperglycemic condition, competition for NADPH between AKR1B1 and GR depletes GSH, and consequently, oxidative stress is increased because GSH is one of the major cellular antioxidants. However, the increased oxidative stress from short-term (days) exposure to hyperglycemia does not cause cell death, only long-term diabetes (months, years) leads to vascular dysfunction and diabetic complications. This may be due to two reasons: (a) in most cells the level of AKR1B1 is not high, (b) glucose is not a good substrate for AKR1B1, and consequently depletion of NADPH is slow. Therefore, even in hyperglycemic state the depletion of GSH is slow, causing only mild oxidative stress. Cancer cells that overexpress AKR1B1 and/or AKR1B10 can be specifically killed by chemical compounds that are efficiently reduced by these enzymes.

Whereas others proposed to inhibit AKR1B1/AKR1B10's activities to stop cancer growth, the methods disclosed herein make use of the activities of these two enzymes to kill cancer cells. In cancer cells that overexpress these two enzymes, administration of their preferred substrates, as disclosed herein, quickly depletes NADPH and consequently, GSH is quickly depleted, leading to severe oxidative stress. Therefore good substrates for AKRs can be used to specifically kill cancer cells that overexpress one or more of these enzymes.

Methods

This disclosure provides a method of treating cancer in a human patient in need thereof, comprising administering a therapeutically effective amount of a substrate of AKR1B1, AKR1B10, or both, to the patient; the patient has, or is suspected to have, cancer cells with elevated levels of AKR1B1, AKR1B10, or both; and the substrate is not 2-deoxy-D-glucose. In certain embodiments, this method further comprises administering a therapeutically effective amount of an inhibitor of reduced glutathione (GSH) to the patient.

Methods exist to detect a patient's cancer cells with elevated levels of AKR1B1, AKR1B10, or both.

This disclosure also provides a method of treating cancer in a human patient in need thereof, comprising administering to the patient a therapeutically effective amount of an activator of AKR1B1 enzyme level or activity, AKR1B10 enzyme level or activity, or the enzyme level or activity of both, in a cancer cell; and administering a therapeutically effective amount of a substrate of AKR1B1, AKR1B10, or both, to the patient; the substrate is not 2-deoxy-D-glucose. In certain embodiments, the substrate is not 2-fluorodeoxy-D-glucose (2FDG).

In certain embodiments, the substrate of AKR1B1, AKR1B10, or both, is D-Galactose, DL-Glyceraldehyde, Diacetyl, Methyglyoxal, Pyridine-2-aldehyde, p-Nitrobenzaldehyde, Pyruvic acid, Progesterone, Prostaglandin E, methyl glyoxal, or 4-hydroynonenal. Any substrate of AKR1B1, AKR1B10, or both, may be used. In certain embodiments, the substrate for use in the disclosed method is a better substrate of AKR1B1, AKR1B10, or both, than 2-DG.

In certain embodiments, the method further comprises treating the patient with a therapeutically effective amount of an activator of AKR1B1 enzyme level or activity, AKR1B10 enzyme level or activity, or the enzyme level or activity of both. In certain further embodiments, the method further comprises treating the patient with an inhibitor of reduced glutathione (GSH).

In some embodiments, the inhibitor of GSH is L-buthionine-[S,R]-sulfoximine (BSO). Any inhibitor of GSH may be used.

In certain embodiments, the activator of AKR1B1 enzyme level or activity, AKR1B10 enzyme level or activity, or the enzyme level or activity of both, is MG-132 or bortezomib. Any activator of AKR1B1 enzyme level or activity, AKR1B10 enzyme level or activity, or the enzyme level or activity of both, may be used.

In certain embodiments, the patient is being treated with one or more other anti-cancer therapy or therapeutic agent. Radiation therapy is an example of a one or more other anti-cancer therapy; traditional chemotherapeutic agents, such as cis-platin, 5-flurouracil, etc., as well as experimental chemotherapeutic agents, are examples of one or more other therapeutic agent. Any other suitable anti-cancer therapy or therapeutic agent may be used, including 5-fluorouracil, doxorubicin, cisplatin, cyclophosphamide, and herceptin TNF-related apoptosis ligands, histone deacetylase inhibitors, and radiation therapy.

In certain embodiments, the cancer is liver, prostate, breast, ovarian, cervical, rectal, lung, or oral cancer. Any cancer that over expresses or may be induced (activated) to over express AKR1B1, AKR1B10, or both, may be treated.

In certain embodiments, a therapeutically effective amount of a substrate of AKR1B1, AKR1B10, or both, an activator of AKR1B1 enzyme level or activity, AKR1B10 enzyme level or activity, and/or an inhibitor of reduced glutathione (GSH) may include an amount (or various amounts in the case of multiple administration) that improves the patient's chance of survival. In certain embodiments, a disclosed method improves the life expectancy of a patient by any amount of time, including at least one day, at least one week, at least two weeks, at least three weeks, at least one month, at least two months, at least three months, at least 6 months, at least one year, at least 18 months, at least two years, at least 30 months, or at least three years, or the duration of treatment.

In certain embodiments, a therapeutically effective amount of a substrate of AKR1B1, AKR1B10, or both, an activator of AKR1B1 enzyme level or activity, AKR1B10 enzyme level or activity, and/or an inhibitor of reduced glutathione (GSH) may include an amount (or various amounts in the case of multiple administration) that reduces a patients' cancer size or the number of cancer cells, or prevent metastasis or further metastasis. Methods exist in the art to assess a patient's survival and his/her state of disease (cancer).

Pharmaceutical Compositions and Formulations

Compositions containing a substrate of AKR1B1, AKR1B10, or both, an activator of AKR1B1 enzyme level or activity, AKR1B10 enzyme level or activity, and/or an inhibitor of reduced glutathione (GSH), can be formulated as a pharmaceutical composition for administering to a subject. Any suitable pharmaceutical compositions and formulations, as well as suitable methods for formulating and suitable routes and suitable sites of administration, are within the scope of this invention, and are known in the art. Also, unless otherwise stated, any suitable dosage(s) and frequency of administration are contemplated.

The pharmaceutical compositions can include a pharmaceutically acceptable carrier (i.e., an excipient). A "pharmaceutically acceptable carrier" refers to, and includes, any and all solvents, dispersion media, coatings, antibacterial and antifungal agents, isotonic and absorption delaying agents, diluent, glidant, etc. The compositions can include a pharmaceutically acceptable salt, e.g., an acid addition salt or a base addition salt (see e.g., Berge et al. (1977) *J Pharm Sci* 66:1-19). The composition can be coated when appropriate.

The substrate of AKR1B1, AKR1B10, or both, an activator of AKR1B1 enzyme level or activity, AKR1B10 enzyme level or activity, and/or an inhibitor of reduced glutathione (GSH), can be formulated at any desired concentration, including relatively high concentrations in aqueous pharmaceutical solutions.

The plasma concentration in a patient, whether the highest level achieved or a level that is maintained, of a substrate of AKR1B1, AKR1B10, or both, an activator of AKR1B1 enzyme level or activity, AKR1B10 enzyme level or activity, and/or an inhibitor of reduced glutathione (GSH) can be any desirable or suitable concentration. Such plasma concentration can be measured by methods known in the art.

An aqueous solution can have a neutral pH, e.g., a pH between, e.g., about 6.5 and about 8 (e.g., between and inclusive of 7 and 8). The aqueous solution can have a pH of about any of the following: 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) about 6 (e.g., greater than or equal to about any of the following: 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than about pH 8.

In some embodiments, a substrate of AKR1B1, AKR1B10, or both, an activator of AKR1B1 enzyme level or activity, AKR1B10 enzyme level or activity, and/or an inhibitor of reduced glutathione (GSH), is administered intravenously to the subject (the term "subject" is used herein interchangeably with the term "patient"), including by intravenous injection or by intravenous infusion. In some embodiments, the substrate of AKR1B1, AKR1B10, or both, the activator of AKR1B1 enzyme level or activity, AKR1B10 enzyme level or activity, and/or the inhibitor of reduced glutathione (GSH), is administered to the lungs of the subject. In some embodiments, the substrate of AKR1B1, AKR1B10, or both, the activator of AKR1B1 enzyme level or activity, AKR1B10 enzyme level or activity, and/or the inhibitor of reduced glutathione (GSH), is administered to the subject by subcutaneous injection. In some embodiments, the substrate of AKR1B1, AKR1B10, or both, the activator of AKR1B1 enzyme level or activity, AKR1B10 enzyme level or activity, and/or the inhibitor of reduced glutathione (GSH), is administered to the subject by way of intraarticular injection. In some embodiments, the substrate of AKR1B1, AKR1B10, or both, the activator of AKR1B1 enzyme level or activity, AKR1B10 enzyme level or activity, and/or the inhibitor of reduced glutathione (GSH), is administered to the subject by way of intravitreal or intraocular injection. In some embodiments, the substrate of AKR1B1, AKR1B10, or both, the activator of AKR1B1 enzyme level or activity, AKR1B10 enzyme level or activity, and/or the inhibitor of reduced glutathione (GSH), is administered to the subject by pulmonary delivery, such as by intrapulmonary injection. Additional suitable routes of administration are also contemplated.

In some embodiments, the methods described herein can include administering to the subject one or more additional treatments, such as one or more additional therapeutic agents. The additional treatment can be any additional treatment, including anti-cancer treatment, therapy, or agent, which includes experimental treatments, or a treatment for a symptom of the cancer, such as fever, etc. The other treatment can be any treatment or any therapeutic agent that improves or stabilizes the patient's health. The additional therapeutic agent(s) includes IV fluids, such as water and/or saline, acetaminophen, heparin, one or more clotting factors, antibiotics, etc. In certain embodiments, the patient is being treated with one or more other anti-cancer therapy or therapeutic agent. Radiation therapy is an example of a one or more other anti-cancer therapy; traditional chemotherapeutic agents, such as cis-platin, 5-flurouracil, etc., as well as experimental chemotherapeutic agents, are examples of one or more other therapeutic agent. Any other suitable anti-cancer therapy or therapeutic agent may be used, including 5-fluorouracil, doxorubicin, cisplatin, cyclophosphamide, and herceptin TNF-related apoptosis ligands, histone deacetylase inhibitors, and radiation therapy.

The one or more additional therapeutic agents, therapy, or treatment, can be administered together with the substrate of AKR1B1, AKR1B10, or both, the activator of AKR1B1 enzyme level or activity, AKR1B10 enzyme level or activity, and/or the inhibitor of reduced glutathione (GSH), as separate therapeutic compositions or one therapeutic composition can be formulated to include both: (i) one or more substrate of AKR1B1, AKR1B10, or both, activator of AKR1B1 enzyme level or activity, AKR1B10 enzyme level or activity, or inhibitor of reduced glutathione (GSH), and (ii) one or more additional therapeutic agents. An additional therapeutic agent or therapy/treatment can be administered prior to, concurrently, or after administration of the substrate of AKR1B1, AKR1B10, or both, the activator of AKR1B1 enzyme level or activity, AKR1B10 enzyme level or activity, and/or the inhibitor of reduced glutathione (GSH). An additional agent and the substrate of AKR1B1, AKR1B10, or both, the activator of AKR1B1 enzyme level or activity, AKR1B10 enzyme level or activity, and/or the inhibitor of reduced glutathione (GSH), can be administered using the same delivery method or route or using a different delivery method or route.

In some embodiments, the substrate of AKR1B1, AKR1B10, or both, the activator of AKR1B1 enzyme level or activity, AKR1B10 enzyme level or activity, and/or the inhibitor of reduced glutathione (GSH), can be formulated with one or more additional active agents useful for treating a cancer in a patient.

When In some embodiments, the substrate of AKR1B1, AKR1B10, or both, the activator of AKR1B1 enzyme level or activity, AKR1B10 enzyme level or activity, and/or the inhibitor of reduced glutathione (GSH), is to be used in combination with a second active agent, the agents can be formulated separately or together. For example, the respective pharmaceutical compositions can be mixed, e.g., just prior to administration, and administered together or can be administered separately, e.g., at the same or different times, by the same route or different route.

The compositions can be administered to a subject, e.g., a human subject, using a variety of methods that depend, in part, on the route of administration. The route can be, e.g., intravenous ("IV") injection or infusion, subcutaneous ("SC") injection, intraperitoneal ("IP") injection, pulmonary delivery such as by intrapulmonary injection (especially for pulmonary sepsis), intraocular injection, intraarticular injection, intramuscular ("IM") injection, or any other suitable route.

A suitable dose of the substrate of AKR1B1, AKR1B10, or both, the activator of AKR1B1 enzyme level or activity, AKR1B10 enzyme level or activity, and/or the inhibitor of reduced glutathione (GSH), which dose is capable of treating cancer in a subject, can depend on a variety of factors including, e.g., the age, gender, and weight of a subject to be treated and the particular compound used. Other factors affecting the dose administered to the subject include, e.g., the type or severity of the cancer. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

In some embodiments, the substrate of AKR1B1, AKR1B10, or both, the activator of AKR1B1 enzyme level or activity, AKR1B10 enzyme level or activity, and/or the inhibitor of reduced glutathione (GSH), can be administered as a fixed dose, or in a milligram per kilogram (mg/kg) dose.

A pharmaceutical composition can include a therapeutically effective amount of the substrate of AKR1B1, AKR1B10, or both, the activator of AKR1B1 enzyme level or activity, AKR1B10 enzyme level or activity, or the inhibitor of reduced glutathione (GSH). Such effective amounts can be readily determined by one of ordinary skill in the art.

The terms "therapeutically effective amount" or "therapeutically effective dose," or similar terms used herein are intended to mean an amount of the substrate of AKR1B1, AKR1B10, or both, the activator of AKR1B1 enzyme level or activity, AKR1B10 enzyme level or activity, or the inhibitor of reduced glutathione (GSH), that will elicit the desired biological or medical response.

EXAMPLES

For this invention to be better understood, the following examples are set forth. These examples are for purposes of illustration only and are not be construed as limiting the scope of the invention in any manner.

Example 1

Proof of Concept

Material and Methods:
Reagents

2-Doxy-d-Glucose (2DG), NADPH, glyceraldehyde, diacetyl, DL-buthionine-sulfoximine (BSO), N-acetyl-cysteine (NAC), MTT assay kits, MG-132, anti-β-actin antibody, goat anti-rabbit secondary antibody and goat anti-mouse secondary antibody were purchased from Sigma (St. Louis, Mo.). Fetal bovine serum (FBS), trypsin, penicillin-streptomycin-neomycin (PSN), DMEM, 1640 and McCoy's 5A were purchased from Gibco. Anti-AKR1B10 antibodies was purchased from Abcom. Bortezomib was purchased from BioVision (Milpitas, Calif.). Tolrestat was purchased from Biochempartner. GSH assay kit was purchased from NanJingJianCheng Bioengineering Institute (Nanjing, Jiansu, China). Anti-AKR1B1 antibodies was a gift from Dr. Deliang Cao of Southern Illinois Medical School. Fidarestat was a gift from Prof. SK Chung of The University of Hong Kong.

Cell Culture

HepG2 cells, SKOV3 cells, HCT116 cells and CaCo2 cells were cultured in DMEM medium, SW480 cells in 1640 medium, and HT29 cells in McCoy's 5A medium. All cell culture media were supplemented with 10% FBS, 1% PSN, and cells were cultured in a humidified incubator containing 5% CO2 at 37° C. In cytotoxicity assays, cells were seeded at 1×105 cells/well in 96 well plates with full medium. In GSH assay and Western blot analysis, cells were seeded at $3 \times 10^6$ cells/well in 6 well plates.

Cytotoxicity Assay

The AKR1Bs substrates' cytotoxicity was assessed by cell survival rate using MTT assay. After the cells were treated with the substrates for the length of time indicated, MTT was added to a final concentration of 0.5 mg/ml in each well of a 96-well plate, and the plates were incubated at 37° C. for 4 hour. Then DMSO was added to dissolve the formazan product, the amount of which is proportional to the number of live cells. The absorbance of dissolved dye was measured at 540 nm using an automatic microplate reader.

Protein Assay

Protein concentration was determined using the Bio-Rad protein assay kit (Bio-Rad Laboratories) according to the manufacturer's protocol.

Western Blot

Cells were lysed on ice with the protein extraction reagent. Total protein (30 μg) per sample were loaded onto 10% SDS-polyacrylamide gels and separated at 75V, and then electrotransferred to polyvinylidene difluoride (PVDF) membranes were then soaked in 5% nonfat milk in TBS at room temperature for 1 hour and then incubated with rabbit anti-AKR1B1 antibodies (1:3000) or rabbit anti-AKR1B10 antibodies (1:3000) at room temperature for 2 hours. After being washed, the membranes were incubated in HRP-conjugated goat anti-rabbit or goat anti-mouse IgG secondary antibodies (1:5000) for 1 hour at room temperature, followed by washing and incubation with ECL reagents for 1 min. β-actin monoclonal mouse antibodies (1:5000) was used as reference to assess the relative amounts of proteins loaded per lane.

GSH Assay

The cells were washed in cold PBS and then scraped into 300 μL of PBS. The cells were disrupted by ultrasonicator on ice followed by centrifuged at 3500 rpm at 4° C. The supernatant was transferred to a fresh tube and used for GSH assay using GSH assay kit. The concentrations of GSH in cell lysates were determined using the standard GSH calibration curve. The GSH detection for each sample was performed at least three times.

Enzyme Activity Assay

Assay of AKR1B1 and AKR1B10 enzymes activities were conducted in 1 ml of the reaction mixture containing 135 mM sodium phosphate buffer (pH 6.2 for AKR1B1 or pH 7.0 for AKR1B10), 0.2 mM NADPH, 0.3 M ammonium sulfate, 2 μg purified protein and 20 mM of their substrate as indicated. The reaction mix was incubated at 30° C. for 30 minutes (min). Protein-free blank controls were included. The decrease of NADPH was monitored by spectrophotometer at 340 nm. Enzyme activity was calculated as the amount of NADPH oxidized/min/mg of protein (Shen Y et al., *Chem Biol Interact.* 2011, 191(1-3): 192-198).

Acute Toxicity Test

ICR mice (18-22 g) were acquired from the Laboratory Animal Services Centre, The Chinese University of Hong Kong. These animals were housed in an animal room with 12 h of day and dark cycles, and the temperature maintained at around 25° C. There were 4 male and 4 female in each treatment and control group. They were treated with either diacetyl or glyceraldehyde. Diacetyl and glyceraldehyde were dissolved with saline and administered to the mice by intravenous injection with the amount indicated. A single injection was administered daily for 14 days, and mice were observed for signs of unusual behavior for 30 minutes after injection. Mortality was recorded daily for the calculation of mean lethal dose (LD50). All surviving animals were euthanized with diethyl-ether at the end of the experiment.

Tumor Xenograft Studies

Six-week-old male BALB/C nude mice were purchased from the Laboratory Animal Unit of the University of Hong Kong. Mice were allowed to acclimate to laboratory conditions for 1 week before cancer cells injection. Human HepG2 tumor xenografts were established by injecting 5×106 HepG2 cell/mice in the right flanks of the nude mice. Treatment was initiated when the tumor grew to about 200±100 mm3. Each treatment group has at least six mice. Mice were randomized and allocated to different groups. They received daily tail vein injection for 3 weeks of one of the following: glyceraldehyde (500 mg/kg body weight); diacetyl (80 mg/kg body weight); or normal saline. Mice were weighted and the sizes of the tumors were measured with calipers every 3 days. Tumor volumes were calculated with the formula: length×width2/2. Animals were humanely killed at the end of the experiment and their tumors were weighed.

Statistical Analysis

Data from all experiments were analyzed by one-way analysis of variance. Statistical significance was defined as $P<0.05$.

Results:

Cells with Higher Levels of AKR1Bs Were More Sensitive to 2DG

To determine the relationship between sensitivity to 2DG toxicity and cellular levels of AKR1Bs, several cell lines (HepG2, SKOV3, HCT116, CaCo2, HT29 and SW480) were examined to determine their sensitivity to 2DG and their expression levels of these two enzymes. As shown in FIG. 1A, HT29 and SW480 were more resistant to 2DG whereas HepG2, SKOV3, HCT116, and CaCo2 were more sensitive. Western blot analysis showed that the resistant cells, HT29 and SW480, had lower levels of AKR1B1 and AKR1B10, and 2DG sensitive cells HCT116 and CaCo2 had high levels of AKR1B1. The other 2DG sensitive cells, HepG2 and SKOV3, had high levels of both AKR1B1 and AKR1B10 (FIG. 1B and FIG. 1C).

Inhibition of AKR1Bs Protects the Cells Against the Toxic Effects of 2DG

Figure 2:
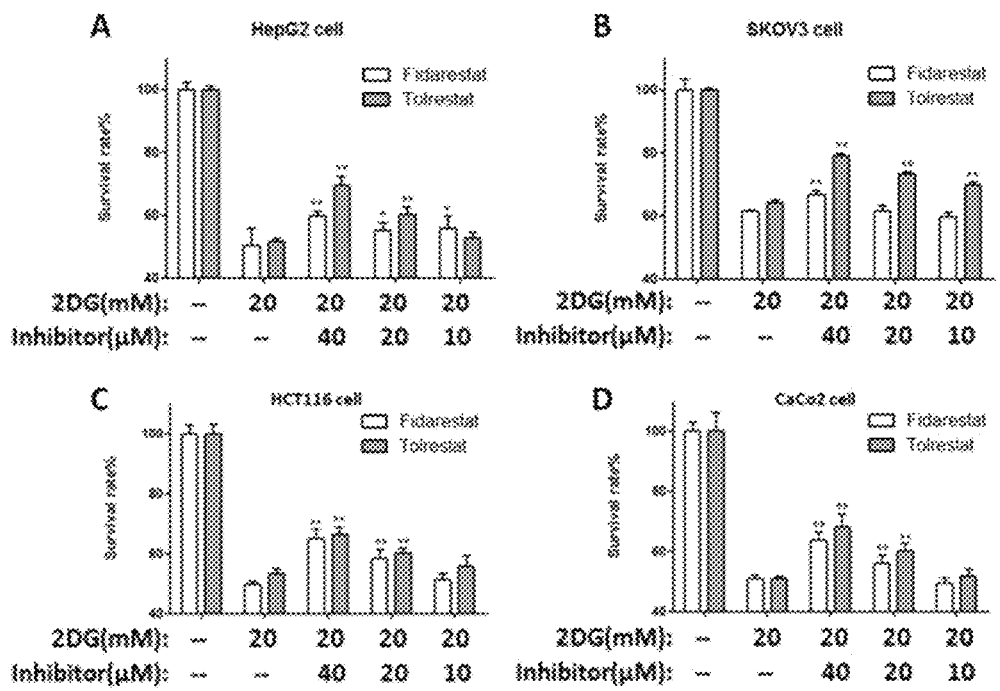
FIG. 2. AKR1Bs inhibitors protect cancer cells against 2DG toxicity. Cells were treated with the inhibitors for 24 hours (h), followed by the addition of 2DG (20 mM) for an additional 48 h. MTT absorbance was measured by recording absorbance at 560 nm.

To confirm that 2DG cytotoxicity was due to the enzymatic activities of AKR1B1 and/or AKR1B10, the effect of inhibition of AKR1B1 and AKR1B10 on cell survival in the presence of 2DG was examined. Two types of AKR1Bs inhibitors, tolrestat and fidarestat, were used. Tolrestat is able to inhibit both AKR1B1 and AKR1B10, whereas fidarestat can only inhibit AKR1B1. As shown in FIG. 2 tolrestat dose-dependently protected all four cell lines against 2DG toxicity, whereas fidarestat protected HCT116 and CaCo2 cells, but less effective in protecting HepG2 and SKOV3 cells. This is most likely due to the fact that HepG2 and SKOV3 overexpress both AKR1B1 and AKR1B10, and AKR1B10 remained active in the presence of fidarestat.

GSH Level in 2DG Treated Cells was Restored by AKR1Bs Inhibitor

Figure 3:
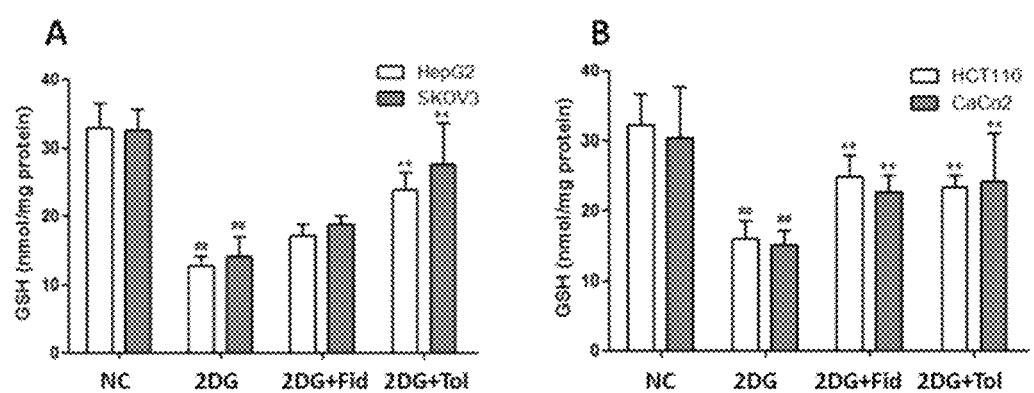
FIG. 3. GSH level is restored by AKR1Bs inhibitor in 2DG treated cells. Cells were treated with the inhibitors (40 µM) for 24 h, followed by the addition of 2DG (20 mM) for an additional 48 h. GSH absorbance was measured by recording the absorbance at 450 nm.

Earlier reports has established that the toxic effect of 2DG in cancer cells is associated with depletion of GSH leading to oxidative stress, although the mechanism is not entirely clear (Li L et al., *Redox Biol.* 2015, 4:127-135. PMID: 25560241; Scarbrough P M et al., *Free Radic Biol Med.* 2012, 15; 52(2):436-443. PMID: 22100505). If 2DG toxicity in cancer cells is mediated by AKR1Bs activities, inhibition of the activities of these two enzymes should attenuate the 2DG-induced depletion of GSH. As shown in FIG. 3, the GSH levels in all four cell lines that are sensitive to 2DG (HepG2, SKOV3, HCT116 and CaCo2) decreased significantly in the presence of 2DG. Tolrestat significantly restored the GSH levels in all four cell lines treated with 2DG. Fidarestat was able to increase the levels of GSH in HCT116 and CaCo2 cells, but not in the HepG2 and SKOV3 cells, presumably because it was not able to inhibit AKR1B10 in these two cell lines.

Figure 4:
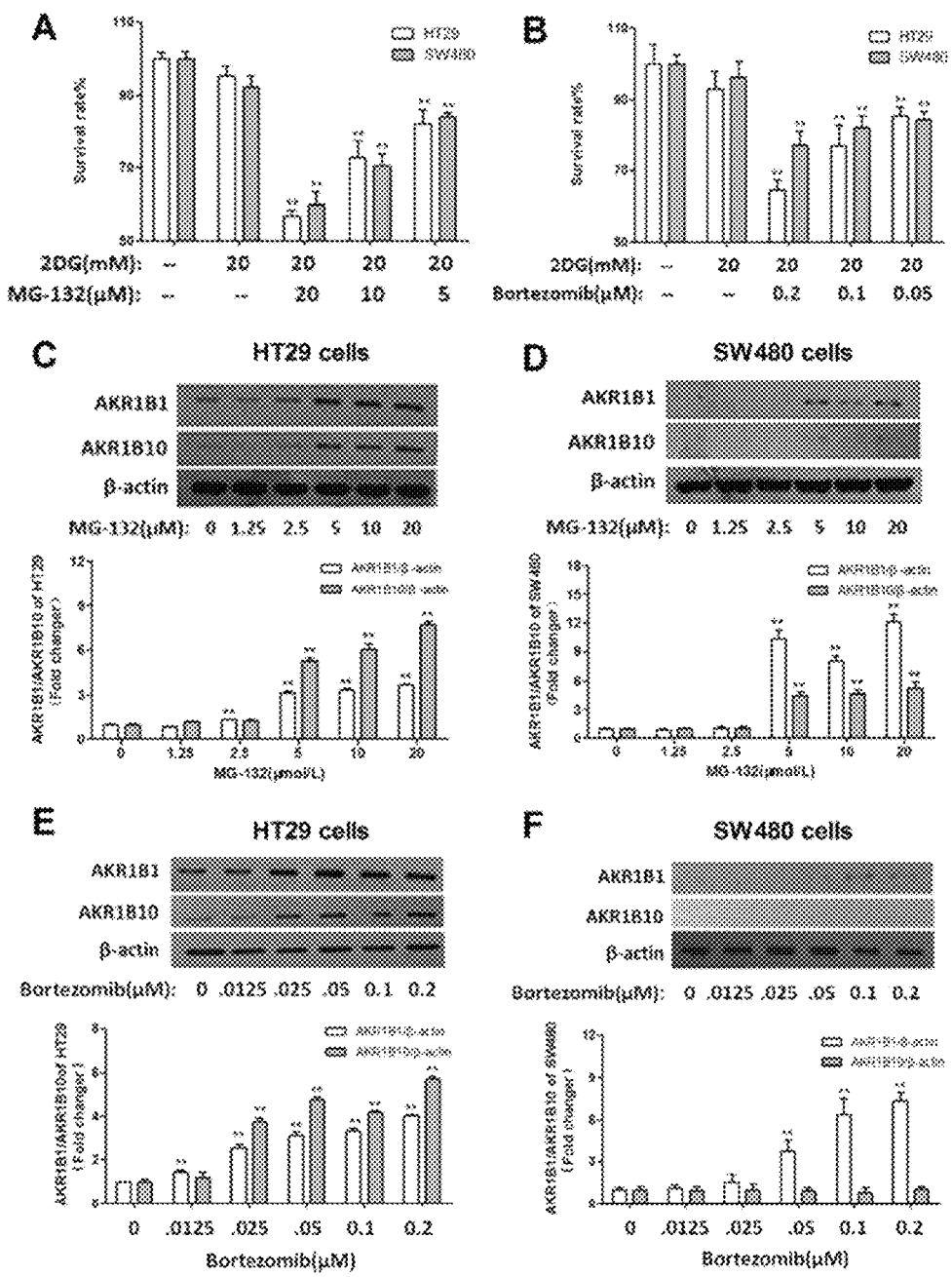
FIG. 4. Increasing the cellular levels of AKR1Bs made the cells more sensitive to 2DG. Cells were treated with MG-132 or bortezomib for 24 h before the addition of 2DG. Bars represent mean±SEM (n=5), p<0.01 versus 2DG group.

Increasing the Cellular Levels of AKR1Bs Rendered the Cells More Sensitive to 2DG To further confirm that sensitivity to 2DG toxicity is due to overexpression of AKR1Bs, the two cell lines (HT29 and SW480) that have low levels of these two enzymes were treated with MG-132 and bortezomib. These two compounds were shown to be able to increase the expression levels of AKR1B1 and AKR1B10 (Bettina E. et al., *Chemico-Biological Interactions.* 2011191: 239-249). As shown in FIG. 4C and FIG. 4D, MG-132 was able to increase the protein levels of AKR1B1 and AKR1B10 in HT29 and SW480 cells (FIG. 4C and FIG. 4D). Bortezomib, on the other hand, increased AKR1B1 and AKR1B10 protein levels in HT29 cells, but in SW480 cells, it induced only AKR1B1 (FIG. 4E and FIG. 4F). When cells were pretreated with MG-132 or bortezomib for 24 hours before the addition of 2DG, significantly more cells were killed by 2DG, indicating that increased levels of AKR1Bs made the cells more sensitive to this drug (FIG. 4A, FIG. 4B).

Figure 5:
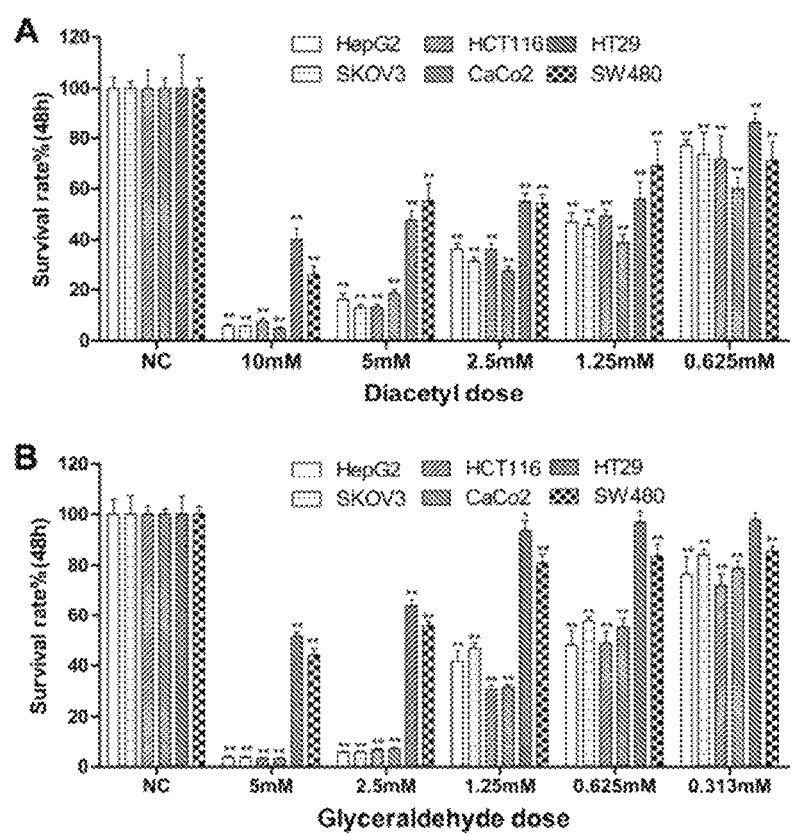
FIG. 5. The cytotoxicity of glyceraldehyde and diacetyl on cancer cells shown in graphs.
Figure 5C:
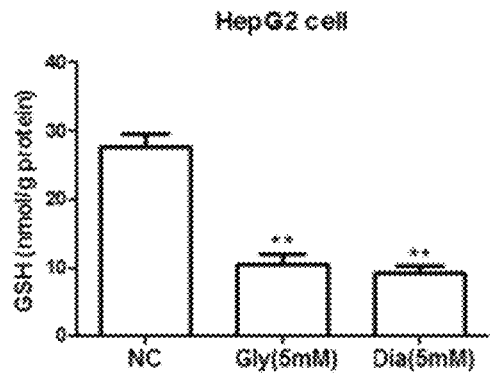
FIG. 5C shows GSH levels in HepG2 cell treated with glyceraldehyde and diacetyl for 48 hours. p<0.01 versus NC group.
Figure 5D:
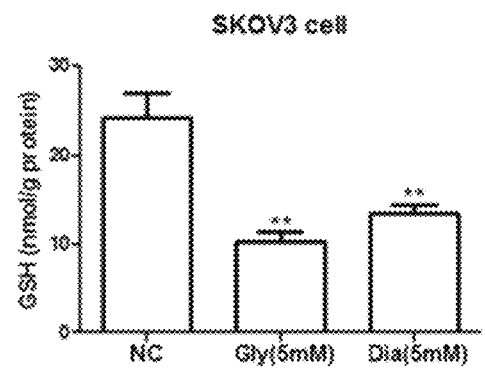
FIG. 5D shows GSH levels in SKOV3 Cell treated with glyceraldehyde and diacetyl for 48 hours. p<0.01 versus NC group.
Figure 5E:
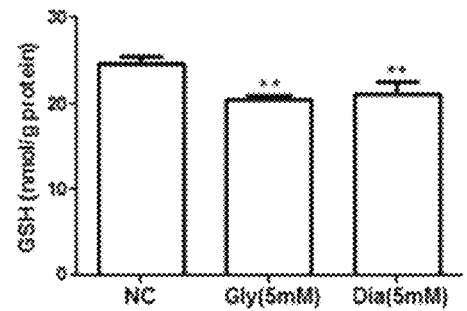
FIG. 5E shows GSH levels in SW480 cell treated with glyceraldehyde and diacetyl for 48 hours. p<0.01 versus NC group.
Figure 5F:
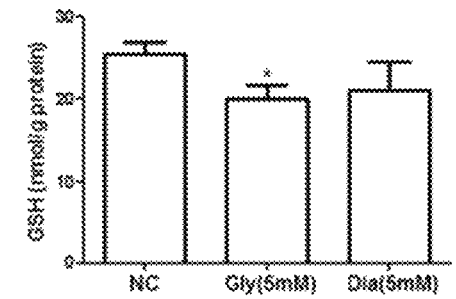
FIG. 5F shows GSH levels in HT29 cell treated with glyceraldehyde and diacetyl for 48 hours. **p<0.05 versus NC group.

Cells that Overexpress AKR1Bs are Also Sensitive to Other Substrates of These Two Enzymes To determine if the mechanism of AKR1Bs-mediate toxicity of 2DG is applicable to other substrates of these two enzymes, Two other substrates of AKR1Bs, glyceraldehyde and diacetyl (Laffin B, Petrash J M. *Front Pharmacol.* 2012, 3:104. PMID: 22685431) were tested. As shown in FIG. 5 both glyceraldehyde and diacetyl dose dependently and preferentially kill cells that have high levels of AKR1Bs (HepG2, SKOV3, HCT116 and CaCo2). Cells (HT29 and SW480) that have low levels of these two enzymes were more resistant to these two substrates.

Figure 5G:
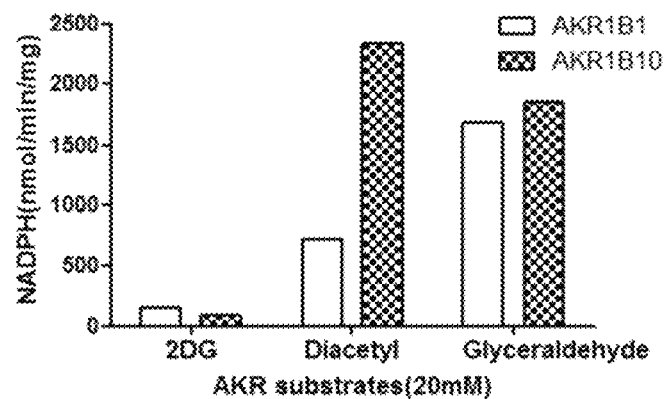
FIG. 5G shows relative efficiency of 2DG, glyceraldehyde and diacetyl being reduced by AKR1B1 and AKR1B10.
Figure 5H:
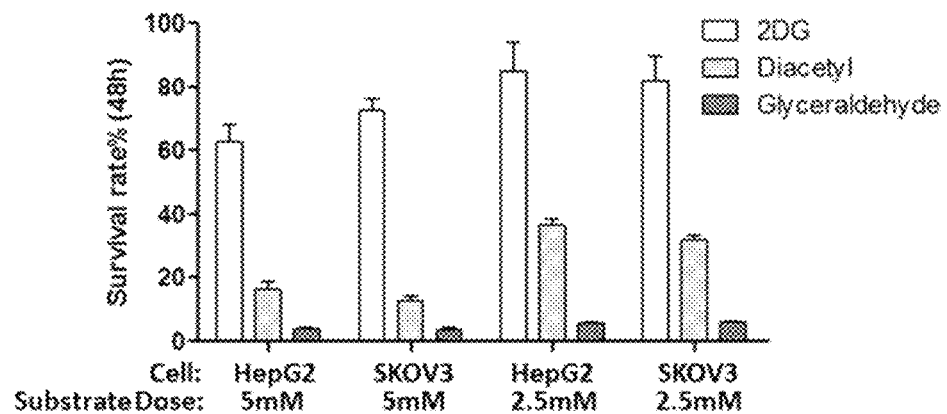
FIG. 5H shows relative efficiency of 2DG, glyceraldehyde and diacetyl in killing HepG2 and SKOV3 cells.
Figure 6:
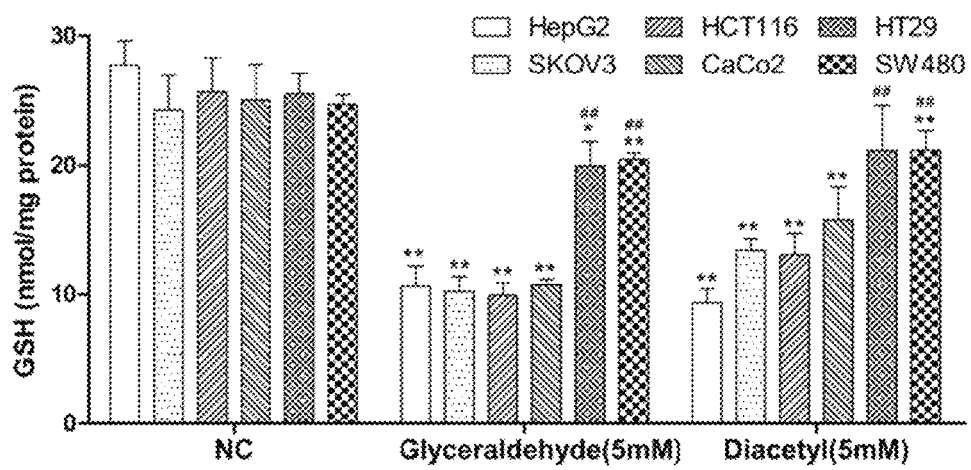
FIG. 6. Depletion of GSH in glyceraldehyde and diacetyl treated cells. GSH levels were measured in treated with glyceraldehyde (5 mM) and diacetyl (5 mM). Bars represent mean±SEM (n=5); *p<0.05 versus; **p<0.01 versus NC group; ##p<0.01 versus HepG2, SKOV3, HCT116 or CaCo2 group.

If the toxicity of the AKR1B1/AKR1B10 substrates is mediated by the activities of these two enzymes, one would expect that the substrates that are more efficiently reduced by these two enzymes should be more toxic to the cells. The efficiency of these compounds serving as substrates for AKR1B1 and AKR1B10 were compared. In enzyme assays detailed in Materials and Methods using commercially available purified AKR1B1 and AKR1B10, comparative efficiency of these two enzymes in reducing 2DG, glyceraldehyde and diacetyl was examined. The activity of these enzymes toward these substrates was measured by the rate of depletion of their co-factor NADPH. As shown in FIG. 5G, 2 DG is the worst substrate among the three for both AKR1B1 and AKR1B10. Glyceraldehyde is an excellent substrate for both AKR1B1 and AKR1B10, whereas diacetyl is a better substrate for AKR1B10 than for AKR1B1. As shown in FIG. 5H glyceraldehyde is most efficient in killing HepG2 and SKOV3, followed by diacetyl, followed by 2DG. The poor substrate 2DG, is not as efficient as glyceraldehyde and diacetyl in killing these cells.

Figure 1:
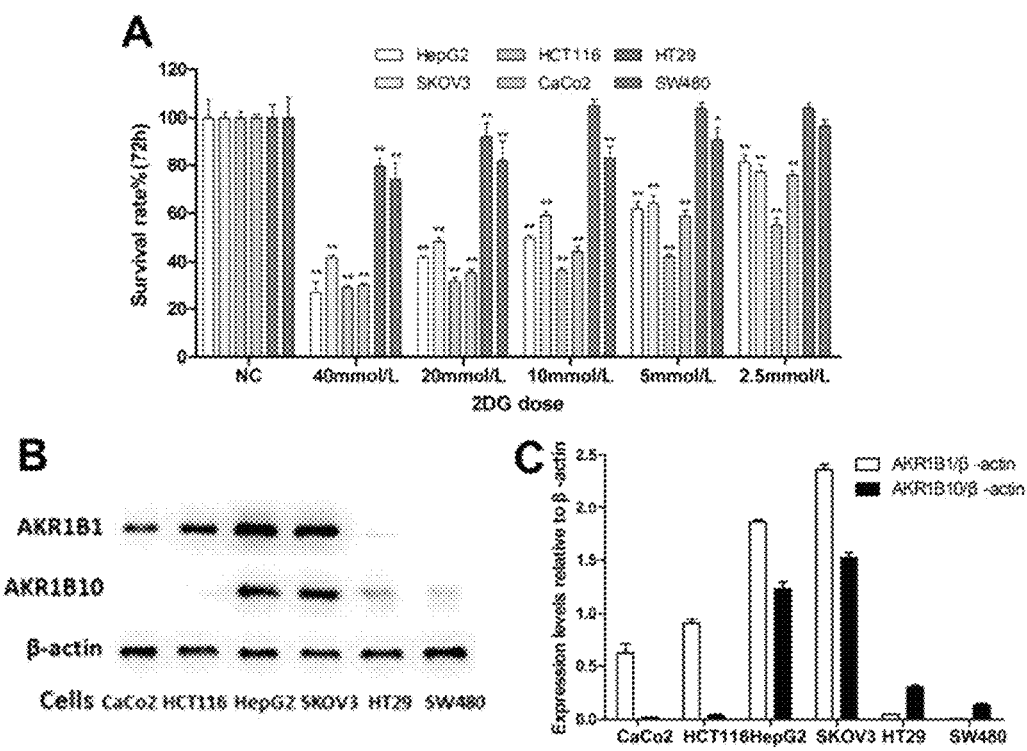
FIG. 1 shows cells' sensitivity to 2DG is correlated to their AKR1Bs protein levels.
Figure 7:
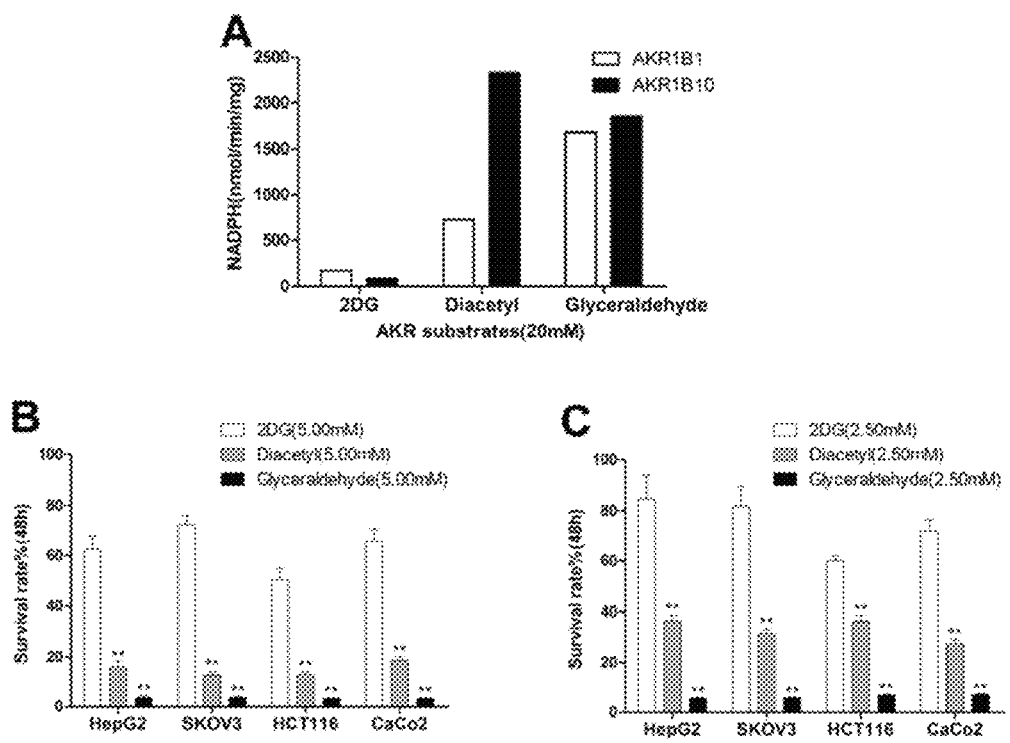
FIG. 7 Cytotoxicity of AKR substrates depends on their catalytic efficiency of AKR1B1 and AKR1B10.

Cytotoxicity of AKR1Bs Substrates Depends on How Efficiently They are Being Reduced by These Enzymes The proposed model of AKR1Bs-mediated cytotoxicity predicts that the better the substrate for these enzymes, the more potent is its cytotoxicity. AKR1Bs' catalytic efficiency for 2DG, glyceraldehyde and diacetyl were compared. These three compounds were used as substrates in standard AKR1B1 and AKR1B10 enzyme assays. Enzyme activities were determined by monitoring the oxidation of the cofactor NADPH. As shown in FIG. 7A, for AKR1B1, glyceraldehyde was the best substrate, followed by diacetyl, then 2DG; for AKR1B10, diacetyl was the best substrate, followed by glyceraldehyde, then 2DG. Data shown in FIG. 1 and FIG. 5 already showed that glyceraldehyde is most toxic to the cells, followed by diacetyl, then 2DG. To ease comparison, the percentages of cells survived after the treatment with these three compounds from FIG. 1 and FIG. 5 are redrawn and shown in figure FIG. 7B and FIG. 7C.

Figure 8:
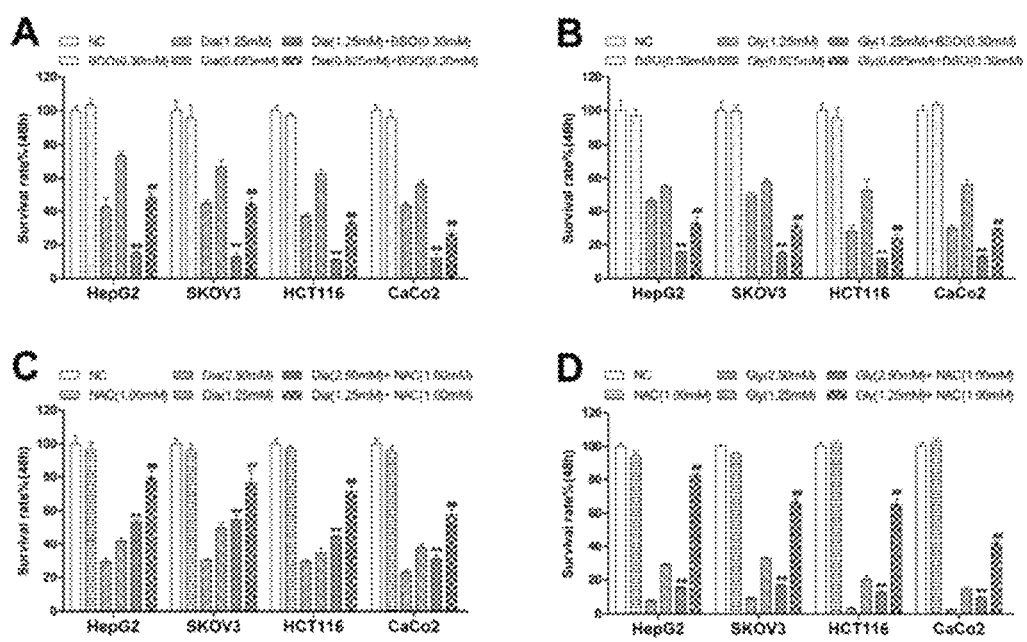
FIG. 8. Cytotoxicity of the AKR1Bs substrates depends on the cellular levels of GSH.

Inhibition of GSH Synthesis Enhanced the Toxicity of AKR1Bs Substrates and Increasing the Levels of GSH Protected the Cells Against Their Toxicity Whether the toxicity of the AKR1Bs substrates is due to the depletion of GSH is tested. This was investigated using glyceraldehyde and diacetyl as their substrates. L-buthionine-[S,R]-sulfoximine (BSO) is a drug that reversibly inhibits glutamate cysteine ligase activity (Sobhakumari A et al. *Plos One,* 2012, 7(10):e48175), and consequently inhibits GSH synthesis, resulting in GSH depletion. As shown in FIG. 8, the presence of BSO enhanced the toxicity of both glyceraldehyde (FIG. 8A) and diacetyl (FIG. 8B) in all four AKR1Bs overexpressing cells. N-acetyl-cysteine (NAC), a precursor of GSH synthesis, was used to increase the cellular concentrations of GSH (Tagde A et al., *Blood Cancer J,*

2014, 4:e229). As shown in FIG. 8C and FIG. 8D, NAC was able to protect the cells against the toxicity of glyceraldehyde and diacetyl in all four cell lines. Taken together, these results strongly support that the AKR1Bs substrates kill cancer cells due to the depletion of their co-factor NADPH, leading to the depletion of GSH and increased oxidative stress.

Inhibition of Glutathione Synthesis Exacerbated the Toxic Effects of AKR1B1/AKR1B10 Substrates If 2DG kills cells that overexpress AKRs because of depletion of GSH, inhibition of GSH synthesis should enhance the toxic effects of 2DG. L-buthionine-[S,R]-sulfoximine (BSO) is a drug that reversibly inhibits glutamate cysteine ligase activity, and consequently inhibits GSH synthesis, resulting in GSH depletion.

Diacetyl and glyceraldehyde, two AKR1B1/AKR1B10 substrates, dose-dependently and preferentially kill HepG2 and SKOV3. As shown in FIG. 9, in the presence of BSO, more HepG2 and SKOV3 cells were killed by diacetyl (FIG. 9A) and glyceraldehyde (FIG. 9B). Thus, the toxicity of AKR1B1/AKR1B10 substrates, 2DG, diacetyl and glyceraldehyde, were all exacerbated by the inhibition of GSH synthesis. FIG. 9B presents results where cell culture and cell survival is same as that described in FIG. 1. In FIG. 9A, BSO exacerbates the toxicity of diacetyl. The amounts of diacetyl used were 1.25 mM and 0.625 mM and the amount of BSO used was 0.3 mM. In FIG. 9B BSO exacerbates the toxicity of glyceraldehyde. The amounts of glyceraldehyde used were 1.25 mM and 0.625 mM and the amount of BSO used was 0.3 mM.

Acute Toxicity of Diacetyl and Glyceraldehyde in Mice

To prepare for the study of the antitumor effects of diacetyl and glyceraldehyde in nude mice xenograft model, the toxicity of these compounds in mice was examined. These compounds were injected into ICR mice as described in Materials and Methods with the amounts indicated in Table 1. From the results shown in Table 1, the LD50 of diacetyl was estimated to be 410 mg/kg body weight. For glyceraldehyde the LD50 was found to be greater than 2000 mg/kg body weight. Because of the solubility problem, higher amounts of glyceraldehyde could not be tested.

TABLE 1

Acute toxicity experiment of diacetyl and glyceraldehyde in mice (n = 8)

| Drugs | Dose (mg/kg BW) | Death/Total | Death Rate % | LD50 (mg/kg BW) |
|---|---|---|---|---|
| Diacetyl | 300 | 0/8 | 0 | 410 |
|  | 360 | 3/8 | 37.5 |  |
|  | 432 | 5/8 | 62.5 |  |
|  | 518 | 7/8 | 87.5 |  |
|  | 622 | 8/8 | 100.0 |  |
| Glyceraldehyde | 1000 | 0/8 | 0 | >2000 |
|  | 2000 | 0/8 | 0 |  |

Tumor Xenograft Studies

To determine the antitumor effects of glyceraldehyde and diacetyl in vivo, HepG2 tumor xenograft in nude mice were developed as described in Materials and Methods. Glyceraldehyde (500 mg/kg) or diacetyl (80 mg/kg) or normal saline were injected into the mice via tail veins daily for 21 days. Tumor size and body weight were measured every 3 days. As shown in FIG. 10B and FIG. 10F, glyceraldehyde and diacetyl did not affect the body weight of the mice. Treatment with glyceraldehyde significantly reduced the tumor volume (FIG. 10C) and tumor weight (FIG. 10D). Similarly, treatment with diacetyl also significantly reduced the tumor volume (FIG. 10G) and tumor weight (FIG. 10H) in nude mice. These results strongly support our hypothesis that substrates of AKR1Bs can be used as anticancer drugs.

A partial list of substrates that has been tested for AKR1B1 and AKR1B10 is shown in Table 2.

TABLE 2

Partial list of substrates reported for AKR1B1 and AKR1B10

| Substrates | AKR1B1 (nmol/min/mg)* | AKR1B10 |
|---|---|---|
| D-Glucose | 129 | 65 |
| D-Galactose | 193 | 65 |
| 2-Deoxyglucose | 149 | 87 |
| DL-Glyceraldehyde | 1681 | 1853 |
| Diacetyl | 725 | 2329 |
| Methyglyoxal | 942 | 7458 |
| Pyridine-2-aldehyde | 632 | 4645 |
| p-Nitrobenzaldehyde | 760 | 4480 |
| Pyruvic acid | ND | ND |
| Progesterone | ND | ND |
| Prostaglandin E | ND | ND |

*Activity is expressed as amount of NADPH (nmol) oxidized per min per mg of protein.
ND means no detectable activity or less than 32 nmol/min/mg.

Discussion

The cancer-specific cytotoxicity of 2DG is due to the depletion of GSH mediated by the activities of AKR1Bs rather than through its inhibition of glycolysis. This is supported by several lines of evidences:

(1) Sensitivity to 2DG toxicity is correlated to the level of expression of AKR1Bs. An anomaly in the results is that CaCo2 and HCT116 that have lower levels of these two enzymes than HepG2 and SKOV3 appeared to be more sensitive to 2DG than HepG2 and SKOV3. It is possible that these two cell lines have lower capacity for de novo synthesis of GSH or have high rate of GSH efflux such that small decreases in GSH regeneration would lead to severe depletion of GSH.

(2) Inhibition of AKR1Bs protected the cells against 2DG toxicity. This is not a non-specific effect of the inhibitors because fidarestat, which only inhibits AKR1B1, was ineffective in protecting cells that overexpress both AKR1B1 and AKR1B10.

(3) Increasing the cellular levels of AK1RBs rendered the cells more sensitive to 2DG.

(4) 2DG induced depletion of GSH was attenuated by AKR1Bs inhibitors.

(5) Other AKR1Bs substrates such as glyceraldehyde and diacetyl also preferentially killed cells that overexpress these two enzymes.

(6) Inhibiting the synthesis of GSH enhanced the toxicity of glyceraldehyde and diacetyl, and conversely, increasing the synthesis of GSH protected the cells against these drugs. These results indicate that similar to 2DG, other AKR1Bs substrates also kill cells by depleting GSH.

(7) The potency of the cytotoxicity of the AKR1Bs substrates is directly correlated to how efficiently they are being reduced by the AKR1Bs.

Two AKR1Bs substrates, glyceraldehyde and diacetyl, were tested in nude mice xenograft tumor model. For convenience, the drugs were administered by daily single dose injection via the tail vein. Although the availability of these drugs in vivo had not been optimized, results showed that they can retard tumor growth. These two drugs, particular glyceraldehyde, are relatively non-toxic. Sustained continuous delivery of these drugs probably would have demonstrated their anticancer effects more dramatically.

The cytotoxicity of 2DG and other AKR1Bs substrates was due to the depletion of GSH. Inhibition of GSH synthesis enhanced their toxicity and increase GSH synthesis protected the cells against their toxic effects. GSH is the major cellular antioxidant, and the importance of the cellular balance of GSH/GSSH ratio in oxidative stress and apoptosis is well recognized. High levels of GSH are associated with resistance to apoptosis, whereas low levels induce apoptosis. It is likely that severe depletion of GSH caused by excessive activities of AKR1Bs would lead to cell death.

GSH also plays a very important role in the development of cancers and in the treatment of cancer. High levels of GSH are required for tumor cell proliferation (Messina J P, Lawrence D A. *J Immun* 1989, 143(6): 1974-1981. PMID: 2789253) and metastasis (Carretero J et al., *Clin Exp Metastasis* 1999, 17(7): 567-574. PMID:10845555). High levels of GSH also confer cancer cells resistance to chemotherapy (Godwin A K et al., *Proc Natl Acad Sci* USA. 1992, 89(7):3070-3074. PMID: 1348364) and radiotherapy (Hanot M et al., *PLoS One*. 2012; 7(11):e44367. PMID:23185232). Various strategies to deplete GSH in cancer cells to sensitize them to chemotherapy and radiotherapy had been suggested, including blocking the regeneration of GSH from GSSH, inhibiting the synthesis of GSH, and increasing the efflux of GSH from cells (Ortega A L, Mena S, Estrela J M. *Cancers (Basel)*. 2011, 3(1): 1285-1310. PMID: 24212662). However, these treatments would also deplete GSH in normal cells, leading to undesirable side effects. Targeted depletion of GSH in cancer cells can be achieved by exploiting the overexpression of AKR1Bs in these cells. In the presence of suitable substrates, their reduction activities would deprive GR of NADPH for its regeneration of GSH. 2DG's augmentation of chemotherapy and radiotherapy is probably based on this mechanism.

Drugs based on the above-described mechanism can be used to treat several types of cancers. AKR1Bs are often overexpressed in a variety of cancers, including liver, prostate, breast, ovarian, cervical, rectal, lung and oral cancers (Cao D et al., *J Biol Chem*. 1998 May 8; 273(19):11429-35; Zeindl-Eberhart E et al., *Hepatology*. 2004 Feb.; 39(2):540-9; Zeindl-Eberhart E et al., *J Biol Chem*. 1994 May 20; 269(20):14589-94; Jin J, Krishack P A, Cao D. *Front Biosci*. 2006 Sep. 1; 11:2767-73; Saraswat M et al., *Med Sci Monit*. 2006 Dec.; 12(12):CR525-529; Fukumoto S et al. *Clin Cancer Res*. 2005 Mar. 1; 11(5):1776-85; Nagaraj N S et al., *Toxicol Lett*. 2006 Aug. 20; 165(2):182-94). The expression levels of these two enzymes in cancers cells vary, ranging from less than 2 fold increase to over 50 fold increase (Laffin B, Petrash J M. *Front Pharmacol*. 2012, 3:104. PMID: 22685431). Those with high levels of one or both of these enzymes would be more susceptible to the toxicity of their substrates. Importantly, it has been reported earlier (Scarbrough P M et al., *Free Radic Biol Med*. 2012, 15; 52(2): 436-443. PMID: 22100505), and demonstrated herein that the level of expression of AKR1Bs can be increased by bortezomid or MG-132. Therefore, even cancer cells with low level of expression of AKR1Bs can be made susceptible to the anticancer effects of their substrates by increasing their levels of expression. This would greatly expand the types of cancer treatable by AKR1Bs substrates. Bortezomid and MG-132 are inhibitors of the ubiquitin-proteosome pathway and had been shown to increase the expression of Nrf2-regulated genes (Dreger H et al., *Cardiovasc*. (2009) 83(2):354-361), among them AKR1B1 and AKR1B10 (Penning T M, Drury J E. *Arch Biochem Biophys*. 2007, 464(2): 241-250). Bortezomid has been used to treat some cancers and to enhance other chemotherapies because improper degradation of regulatory proteins is thought to contribute to cancer growth (Lenz H. J. *Cancer Treat*. (2003) Rev. 29 (Suppl. 1) 41-48). Increased levels of AKR1Bs induced by this drug may contribute to its anti-cancer effect because endogenous metabolites such as methyl glyoxal, and 4-hydroynonenal are excellent substrates for these two enzymes.

A novel anticancer mechanism based on the activities of AKR1Bs is disclosed herein. This would lead to the development of a new class of anticancer drugs. AKR1B1 and AKR1B10 can reduce a broad range of substrates, primarily small molecular weight aldehydes and ketones. Two of their substrates glyceraldehyde and diacetyl have anticancer activity. They should be more effective than 2DG in killing cancer cells. Substrates preferred by AKR1B10 may be better anticancer drug candidates because unlike AKR1B1, which is expressed in all tissues, AKR1B10 is normally only expressed in the small intestine and colon (Busu C et al., *J Med Life*. 2014, 7(4):611-618. PMID: 25713632). This should restrict the potential undesirable side effects of the drugs.

Other Embodiments

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A method of treating cancer in a human patient in need thereof, comprising measuring AKR1B10 level in cancer cells of said patient,
    administering to said patient, a therapeutically effective amount of an activator of AKR1B10 and/or AKR1B1 enzyme level in cancer cells, a therapeutically effective amount of an inhibitor of reduced glutathione (GSH), a therapeutically effective amount of diacetyl or glyceraldehyde to said patient, wherein said patient has cancer cells with elevated levels of AKR1B10;
    said administration of diacetyl or glyceraldehyde resulting in increased oxidative stress in one or more of said cancer cells; measuring reduced glutathione (GSH) enzyme level in said patient's cancer cells to confirm that reduced glutathione (GSH) level has decreased;
    wherein the cancer is liver, prostate, breast, ovarian, cervical, rectal, lung, pancreatic, or oral cancer, wherein the activator of AKR1B10 and/or AKR1B1 enzyme level is MG-132 or bortezomib and wherein the inhibitor of reduced glutathione (GSH) is L-buthionine-[S,R]-sulfoximine (BSO).

2. The method of claim 1, further comprising administering to said patient one or more other anti-cancer therapy or therapeutic agent.

3. The method of claim 2, wherein radiation therapy is one of the one or more other anti-cancer therapy.

4. A method of treating cancer in a human patient in need thereof, comprising measuring AKR1B10 and/or AKR1B1 level in cancer cells of said patient, administering to said patient, a therapeutically effective amount of an activator of AKR1B10 and/or AKR1B1 enzyme level in cancer cells, a therapeutically effective amount of an inhibitor of reduced glutathione (GSH), a therapeutically effective amount of diacetyl or glyceraldehyde to said patient, wherein said patient has cancer cells with elevated levels of AKR1B10 and/or AKR1B1;

said administration of diacetyl or glyceraldehyde resulting in increased oxidative stress in one or more of said cancer cells;

wherein the cancer is liver, prostate, breast, ovarian, cervical, rectal, lung, pancreatic, or oral cancer, wherein the activator of AKR1B10 and/or AKR1B1 enzyme level is MG-132 or bortezomib and wherein the inhibitor of reduced glutathione (GSH) is L-buthionine-[S,R]-sulfoximine (BSO).

5. The method of claim 4, further comprising administering to said patient one or more other anti-cancer therapy or therapeutic agent.

6. The method of claim 5, wherein radiation therapy is one of the one or more other anti-cancer therapy.

7. The method of claim 4, further comprising measuring reduced glutathione (GSH) enzyme level in said patient's cancer cells to confirm that reduced glutathione (GSH) level has decreased.

* * * * *